US008362465B2

(12) United States Patent
Enomoto

(10) Patent No.: US 8,362,465 B2
(45) Date of Patent: Jan. 29, 2013

(54) ORGANIC EL LIGHT-EMITTING MATERIAL AND ORGANIC EL LIGHT-EMITTING ELEMENT

(75) Inventor: Masashi Enomoto, Tokyo (JP)

(73) Assignee: Sony Corporation, Tokyo (JP)

( * ) Notice: Subject to any disclaimer, the term of this patent is extended or adjusted under 35 U.S.C. 154(b) by 140 days.

(21) Appl. No.: 12/545,493

(22) Filed: Aug. 21, 2009

(65) Prior Publication Data

US 2010/0044693 A1    Feb. 25, 2010

(30) Foreign Application Priority Data

Aug. 25, 2008  (JP) ................................ 2008-215587

(51) Int. Cl.
 *H01L 51/00* (2006.01)
(52) U.S. Cl. .............. 257/40; 313/504; 438/82; 438/99; 438/562; 438/623; 438/780
(58) Field of Classification Search ............ 438/82, 438/99, 562, 623, 725, 780, 781; 257/40; 313/504
See application file for complete search history.

(56) References Cited

U.S. PATENT DOCUMENTS

| 3,974,176 | A  | * | 8/1976 | Rainer ...................... 548/374.1 |
| 5,104,749 | A  | * | 4/1992 | Sato et al. .................... 428/690 |
| 7,338,722 | B2 | * | 3/2008 | Thompson et al. ........... 428/690 |
| 7,507,486 | B2 | * | 3/2009 | Ren .............................. 428/690 |
| 7,893,611 | B2 | * | 2/2011 | Umakoshi et al. ............ 313/504 |
| 2002/0134984 | A1 | * | 9/2002 | Igarashi ......................... 257/79 |
| 2004/0137268 | A1 | * | 7/2004 | Igarashi et al. ............... 428/690 |
| 2004/0253478 | A1 | * | 12/2004 | Thompson et al. ........... 428/690 |
| 2005/0123792 | A1 | * | 6/2005 | Deaton et al. ................. 428/690 |
| 2006/0287498 | A1 | * | 12/2006 | Morishita et al. ............. 528/422 |
| 2007/0048546 | A1 | * | 3/2007 | Ren .............................. 428/690 |
| 2009/0102370 | A1 | * | 4/2009 | Taka et al. ..................... 313/504 |
| 2009/0146139 | A1 | * | 6/2009 | Stoessel et al. ................. 257/40 |
| 2009/0302752 | A1 | * | 12/2009 | Parham et al. ................ 313/504 |

FOREIGN PATENT DOCUMENTS

JP    2003-292494    10/2003

OTHER PUBLICATIONS

Omary et al, Metal Effect on the Suramoecular Structure, Photophysics and Acid-Base Character of Trinuclear Pyrazolato Coinage Metal Complexes, American Chemical Society, Inorganic Chemistry.*
Dias et al., A Classical Silver Carbonyl Compund [{MeB[3-(Mes)pz]3}Ag(CO)] and the Related Silver Ethylene Adduct [{MeB[3-(Mes)pz]3}Ag(C2H4)]**, Angewandte Chemie Ed. 2007, 46,2188-2191.*

(Continued)

*Primary Examiner* — N Drew Richards
*Assistant Examiner* — Ankush Singal
(74) *Attorney, Agent, or Firm* — K&L Gates LLP

(57) ABSTRACT

An organic EL light-emitting material and an organic EL light-emitting element using the same are provided. Between an anode and a cathode, there are provided a hole transport layer, a light-emitting layer constituted of an organic EL light-emitting material including at least one kind of metal pyrazole complex constituted of a metal ion that is a monovalent cation of a d10 group element and a pyrazole ligand that has a predetermined substituent at the whole or a part of 3, 4 and 5 sites, and an electron transport layer, in this order from the anode side.

16 Claims, 4 Drawing Sheets

OTHER PUBLICATIONS

Masciocchi et al., The Multiphase Nature of the Cu(pz) and Ag(pz)(Hpz=pyrazole) Systems : Selective Syntheses and Ab-Initio X-ray Powder Diffraction Structural Characterization of Copper(I) and Silver(I) Pyrazolates, J. Am. Chem. Soc. 1994,116,7668-7676.*

Baldo, M.A. et al., "High-efficiency fluorescent organic light-emitting devices using a phosphorescent sensitizer," Nature, vol. 403, pp. 750-753, 2000.

Barbera, J. et al., "(Pyrazolato)gold Complexes Showing Room-Temperature Columnar Mesophases. Synthesis, Properties, and Structural Characterization," Inorg. Chem, vol. 37, pp. 2960-2967, 1998.

Dias, H.V. Rasika, et al., "Bright Phosphorescence of a Trinuclear Copper(I) Complex: Luminescence Thermochromism, Solvatochromism, and "concentration Luminochromism", " J. Am. Chem. Soc., vol. 125, pp. 12072-1273, 2003.

Enomoto, M. et al., "Coordination Metallacycles of an Achiral Dendron Self-Assemble via Metal-Metal Interaction to Form Luminescent Superhelical Fibers," J. Am. Chem. Soc., vol. 123, pp. 5608-5609, 2001.

Grushin, V. et al., "New, efficient electroluminescent materials based on organometallic Ir complexes," Chem. Commun, pp. 1494-1495, 2001.

Kido, J. et al., "Organo Lanthanide Metal Complexes for Electroluminescent Materials," Chem. Rev., vol. 102, pp. 2357-2368, 2002.

Kim, S.J. et al., "Trinuclear Gold(I) Pyrazolate Complexes Exhibiting Hexagonal Columnar Mesophases with Only Three Side Chains," Chem. Mater., vol. 10, pp. 1889-1893, 1998.

Lamansky, S. et al., "Highly Phosphorescent Bis-Cyclometalated Iridium Complexes: Synthesis, Photophysical Characterization, and Use in Organic Light Emitting Diodes," J. Am. Chem. Soc., vol. 123, pp. 4304-4312, 2001.

Tekarli, S.M. et al., "Rational Design of Macrometallocyclic Trinuclear Complexes with Superior $\pi$-Acidity and $\pi$-Basicity," J. Am. Chem. Soc., vol. 130, pp. 1669-1675, 2008.

Xie, H.Z. et al., "Reduction of Self-Quenching Effect in Organic Electrophosphorescence Emitting Devices via the Use of Sterically Hindered Spacers in Phosphorescence Molecules," Adv. Mater., vol. 13, pp. 1245-1248, 2001.

Zhang, J. et al., "Energy transfer from singlet to triplet excited states in organic light-emitting device," Synthetic Metals, vol. 121, pp. 1723-1724, 2001.

* cited by examiner

ORGANIC EL LIGHT-EMITTING MATERIAL AND ORGANIC EL LIGHT-EMITTING ELEMENT

CROSS REFERENCES TO RELATED APPLICATIONS

The present application claims priority to Japanese Priority Patent Application JP 2008-215587 filed in the Japan Patent Office on Aug. 25, 2008, the entire content of which is hereby incorporated by reference.

BACKGROUND

The present application relates to an organic EL light-emitting material and an organic EL light-emitting element, which uses the organic EL light-emitting material, for display devices such as flat light sources and color displays.

In recent years, display devices using an organic electroluminescent element (so-called organic EL light-emitting element) have been attracting attention as a flat panel display with small power consumption, high response speed and no viewing angle dependence.

In general, organic EL light-emitting elements have an organic layer inserted between a cathode and an anode, in which holes and electrons injected from the anode and cathode, respectively, recombine in the organic layer to emit light. As the organic layer, there are developed, for example, such constructions as a stack of a hole transport layer, a light-emitting layer including a light-emitting material, and an electron transport layer in this order from the anode side and a stack of those layers in which an electron transport layer further includes a light-emitting material to work as a light-emitting layer having an electron transport property.

Regarding a light-emitting material, after the announcement of EL emission by means of a phosphorescent compound (iridium complex) by a group of Baldo et. al. in 2000 (See Baldo, M. A.; Thompson, M. E.; Forrest, S. R. Nature 2000, 403, 750-753.), improvements of tris- and bis-cyclometalated iridium (III) complex by chemical modification have energetically been performed (See Lamansky, S.; Djurovich, P.; Murphy, D.; Abdel-Razzaq, F.; Lee, H. E.; Adachi, C.; Burrows, P.; Forrest, S. R.; Thompson, M. E. J. Am. Chem. Soc. 2001, 123, 4304-4312.).

For example, it has come to realize that in fluorinated derivatives, a triplet-triplet quenching process is suppressed and further, sublimation properties of the complex are improved (See Grushin, V. V.; Herron, N.; LeCloux, D. D.; Marshall, W. J.; Petrov, V. A.; Wang, Y. Chem. Commun. 2001, 1494-1495.), and that self-quenching can be suppressed by introducing a group having a large steric hindrance (See Xie, H. Z.; Liu, M. W.; Wang, O. Y.; Zhang, X. H.; Lee, C. S.; Hung, L. S.; Lee, S. T.; Teng, P. F.; Kwong, H. L.; Hui, Z.; Che, C. M. AdV. Mater. 2001, 13, 1245-1248.). In addition, regarding lanthanide-based phosphorescent materials, there are some of materials that are presented in review paper by Kido et. al. (See Kido. J.; Okamoto, Y. Chem. Rev. 2002, 102, 2357-2368.).

However, these complexes use a rare metal and are very expensive, and lack stability.

Regarding EL elements using a copper atom, there is a study of Zhang et. al. (Zhang, J.; Kan, S.; Ma, Y.; Shen, J.; Chan, W,; Che, C. Synth. Met. 2001, 121, 1723-1724), but, no great improvement in emission efficiency is observed.

Further, examples of metal pyrazole complexes have been reported until now in Kim, S. J.; Kang, S. H.; Park, K.-M.; Kim, H.; Zin, W.-C.; Choi, M.-G.; Kim, K. Chem. Mater. 1998, 10, 1889-1893; Barbera, J.; Elduque, A.; Gimenez, R.; Lahoz, F. J.; Lopez, J. A.; Oro, L. A.; Serrano, J. L. Inorg. Chem. 1998, 37, 2960-2967; Enomoto, M.; Kishimura, A.; Aida, T. J. Am. Chem. Soc. 2001, 123, 5608-5609; and Dias, H. V. R.; Diyabalanage, H. V. K.; Rawashdeh-Oary, M. A.; Franzman, M. A.; Omary, M. A. J. Am. Chem. Soc. 2003, 125, 12072-12073. Regarding a metal pyrazole complex, although Enomoto et. al. found strong photoluminescence exhibited by irradiation of ultraviolet rays, there has been no report on EL emission.

SUMMARY

The present application has been completed with the view of the above problems in the related art, and it is desirable to provide an organic EL light-emitting material that is inexpensive and shows high emission efficiency, and an organic EL light-emitting element using the organic EL light-emitting material.

The inventor has found a great improvement in the emission efficiency when a metal pyrazole complex that is constituted of a monovalent cation of a d10 group metal (gold, silver, and copper) and a pyrazole ligand is used in an organic EL light-emitting layer, and as the results of hard studies, has completed the present application.

According to an embodiment, there is provided an organic EL light-emitting material including at least one kind of metal pyrazole complex represented by one of general formulae (1) and (2):

(where, $R_1$,

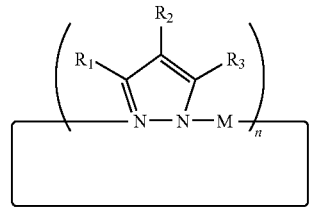

(1)

$R_2$, and $R_3$ independently represent a hydrogen atom, a branched or linear alkyl group having 1 to 18 carbon atoms, a branched or linear halogen-substituted alkyl group having 1 to 18 carbon atoms, a phenyl group, a halogen-substituted phenyl group, a halogen atom, an ester group having 1 to 12 carbon atoms, an alkyl sulfide group, an ether group or an amide group; n represents an integer of 3 to 6; and M is selected from Au, Ag and Cu);

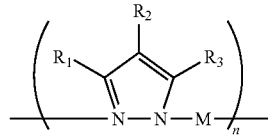

(2)

(where, $R_1$, $R_2$, and $R_3$ independently represent a hydrogen atom, a branched or linear alkyl group having 1 to 18 carbon atoms, a branched or linear halogen-substituted alkyl group having 1 to 18 carbon atoms, a phenyl group, a halogen substituted phenyl group, a halogen atom, an ester group having 1 to 12 carbon atoms, an alkyl sulfide group, an ether group or an amide group; n represents a positive integer, and M is selected from Au, Ag and Cu).

Further, according to another embodiment there is provided an organic EL light-emitting element (organic EL light-emitting element 11) including, between an anode (anode 13) and a cathode (cathode 15) provided on a substrate (substrate 12), a hole transport layer (hole transport layer 14b), a light-emitting layer (light-emitting layer 14c) containing an organic EL light-emitting material including at least one kind of metal pyrazole complex represented by one of general formulae (1) and (2), and an electron transport layer (electron transport layer 14d) in this order from the anode side (FIG. 1): (where,

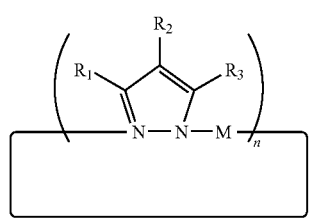

(1)

$R_1$, $R_2$, and $R_3$ independently represent a hydrogen atom, a branched or linear alkyl group having 1 to 18 carbon atoms, a branched or linear halogen-substituted alkyl group having 1 to 18 carbon atoms, a phenyl group, a halogen substituted phenyl group, a halogen atom, an ester group having 1 to 12 carbon atoms, an alkyl sulfide group, an ether group or an amide group; n represents an integer of 3 to 6; and M is selected from Au, Ag and Cu);

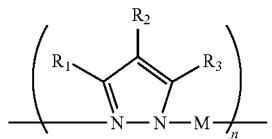

(2)

(where, $R_1$, $R_2$, and $R_3$ independently represent a hydrogen atom, a branched or linear alkyl group having 1 to 18 carbon atoms, a branched or linear halogen-substituted alkyl group having 1 to 18 carbon atoms, a phenyl group, a halogen-substituted phenyl group, a halogen atom, an ester group having 1 to 12 carbon atoms, an alkyl sulfide group, an ether group or an amide group; n represents a positive integer; and M is selected from Au, Ag and Cu).

Here, it is preferable to provide a hole injection layer (hole injection layer 14a) between the anode and the hole transport layer.

When used in a light-emitting layer of an organic EL light-emitting element, the organic EL light-emitting material according to an embodiment can improve the electroconductivity as the organic EL light-emitting element and improve luminance as the result of high emission efficiency.

Additional features and advantages are described herein, and will be apparent from the following Detailed Description and the figures.

DETAILED DESCRIPTION

Figure 1:
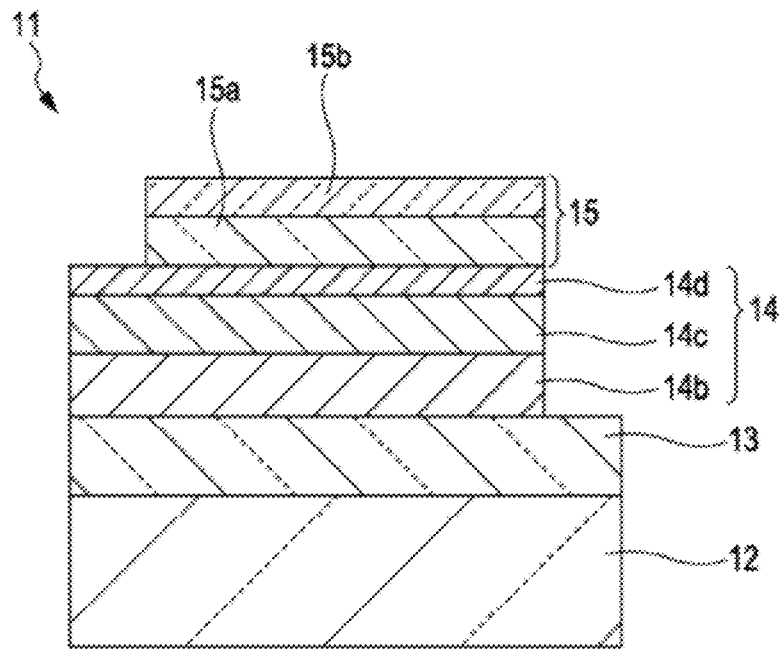
FIG. 1 is a cross-sectional view showing a constitutional example (1) of an organic EL light-emitting element according to an embodiment.

Hereinafter, a construction of an organic EL light-emitting material and an organic EL light-emitting element according to an embodiment of the present application will be described. The present application will be described based on embodiments shown in the drawings.

An organic EL light-emitting material according to an embodiment is a metal pyrazole complex constituted of a monovalent cation of a d10 group element as a metal ion and a pyrazole ligand having a predetermined substituent at the whole or a part of 3, 4 and 5 sites. Specifically, the material is one including at least one kind of cyclic metal pyrazole complex represented by general formula (1).

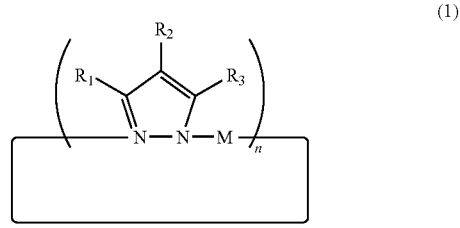

(1)

In the formula (1), $R_1$, $R_2$, and $R_3$ independently represent a hydrogen atom, a branched or linear alkyl group having 1 to 18 carbon atoms, a branched or linear halogen-substituted alkyl group having 1 to 18 carbon atoms, a phenyl group, a halogen-substituted phenyl group, a halogen atom, an ester group having 1 to 12 carbon atoms, an alkyl sulfide group, an ether group or an amide group; n represents an integer of 3 to 6; and M is selected from Au, Ag and Cu.

Alternatively, the organic EL light-emitting material according to an embodiment is one including at least one kind of linear metal pyrazole complex represented by general formula (2) below.

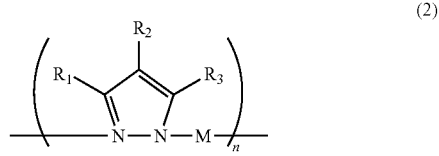

(2)

In the formula (2), $R_1$, $R_2$, and $R_3$ independently represent a hydrogen atom, a branched or linear alkyl group having 1 to 18 carbon atoms, a branched or linear halogen-substituted alkyl group having 1 to 18 carbon atoms, a phenyl group, a halogen-substituted phenyl group, a halogen atom, an ester group having 1 to 12 carbon atoms, an alkyl sulfide group, an ether group or an amide group; n represents a positive integer, and M is selected from Au, Ag and Cu.

Further, an organic EL light-emitting material according to an embodiment is preferably one including at least one kind of cyclic metal pyrazole complex represented by general formula (3) below. That is, one in which n=3 in the above-mentioned formula (1).

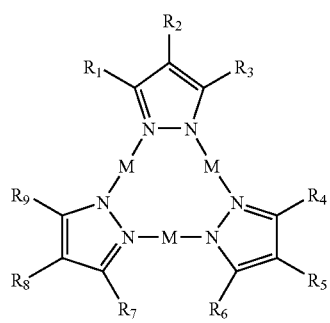

(3)

In the formula (3), $R_1$, $R_2$, $R_3$, $R_4$, $R_5$, $R_6$, $R_7$, $R_8$, and $R_9$ independently represent a hydrogen atom, a branched or linear alkyl group having 1 to 18 carbon atoms, a branched or linear halogen-substituted alkyl group having 1 to 18 carbon atoms, a phenyl group, a halogen-substituted phenyl group, a halogen atom, an ester group having 1 to 12 carbon atoms, an alkyl sulfide group, an ether group or an amide group; and M is selected from Au, Ag and Cu.

Next, an organic EL light-emitting element according to an embodiment will be described.

FIG. 1 is a cross-sectional view schematically representing a constitutional example (1) of an organic EL light-emitting element according to an embodiment. An organic EL light-emitting element 11 shown in the drawing includes an anode 13, an organic layer 14 and a cathode 15 stacked on a substrate 12 in this order. Among these, the organic layer 14 includes, for example, a hole transport layer 14b, a light-emitting layer 14c and an electron transport layer 14d stacked in this order from the anode 13 side.

Figure 2:
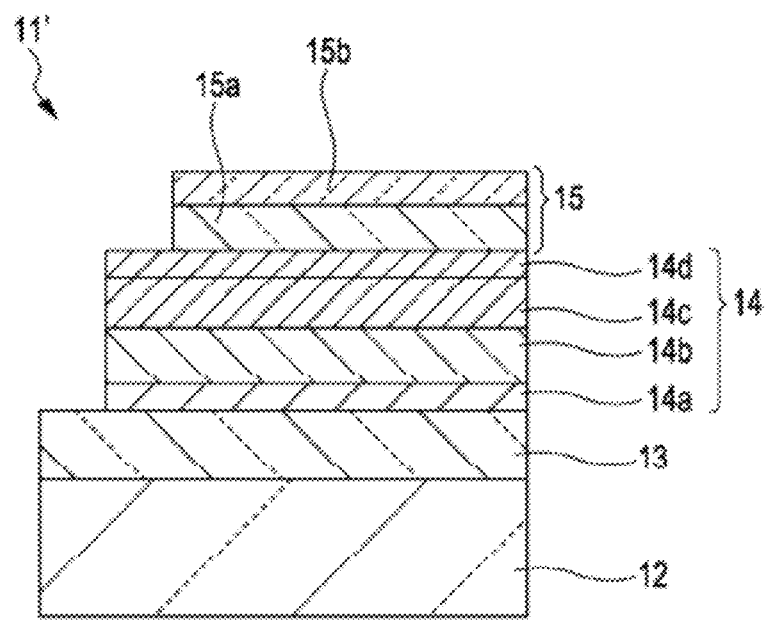
FIG. 2 is a cross-sectional view showing a constitutional example (2) of an organic EL light-emitting element according to an embodiment.

FIG. 2 is a cross-sectional view schematically showing a constitutional example (2) of an organic EL light-emitting element according to another embodiment. An organic EL light-emitting element 11' shown in the drawing includes the anode 13, the organic layer 14 and the cathode 15 stacked in this order on the substrate 12. Among these, the organic layer 14 includes, for example, a hole injection layer 14a, the hole transport layer 14b, the light-emitting layer 14c and the electron transport layer 14d stacked in this order from the anode 13 side.

Next, detailed constructions of respective portions constituting the organic EL light-emitting elements 11, 11' are described in order from the substrate 12 side.

<Substrate>

The substrate 12 is a support including the organic EL light-emitting elements 11, 11' arranged and formed on one main face side thereof, which may be an existing one. For example, quartz, glass, metal foil or a film, sheet and the like made of resin are used. Among these, quartz and glass are preferable. When the substrate 12 is made of resin, the material thereof includes methacrylate resins represented by polymethyl methacrylate (PMMA), polyesters such as polyethylene terephthalate (PET), polyethylene naphthalate (PEN) and polybutylene naphthalate (PBN), and polycarbonate resin. They may have a stacked structure for suppressing water penetration and gas penetration, or have been subjected to surface treatment.

<Anode>

For the anode 13, in order to inject holes efficiently, one having a large work function from the vacuum level of an electrode material is used including, for example, metals such as aluminum (Al), chromium (Cr), molybdenum (Mo), tungsten (W), copper (Cu), silver (Ag) and gold (Au) and alloys thereof, oxides and the like of these metals and alloys; and an alloy of tin oxide ($SnO_2$) and antimony (Sb), iWO (indium tungsten oxide), ITO (indium tin oxide), InZnO (indium zinc oxide), an alloy of zinc oxide (ZnO) and aluminum (Al), and oxide and the like of these metals and alloys, which are used alone or in a mixed state. Among these, a transparent conductive layer of IWO with smooth surface is more preferable.

A drive system used for display devices with the organic EL light-emitting elements 11, 11' may be a passive matrix system or an active matrix system. When the active matrix system is used, the anode 13 is patterned every pixel and provided in such a state as being connected to a driving thin film transistor on the substrate 12. Further, the construction in this case includes an insulating film provided on the anode 13, which is not shown. The surface of anode 13 of each pixel is exposed from an opening of the insulating film.

<Hole Injection Layer/Hole Transport Layer>

Each of the hole injection layer 14a and the hole transport layer 14b is a layer for enhancing the efficiency of a hole injection into the light-emitting layer 14c. Examples of materials that can be used for such hole injection layer 14a or hole transport layer 14b include benzin, styrilamine, triphenylamine, porphyrin, triphenylene, azatriphenylene, tetracyanoquinodimethane, triazole, imidazole, oxadiazole, polyarylalkane, phenylenediamine, arylamine, oxazole, anthracene, fluorenone, hydrazone, stilbene and derivatives thereof, and monomers, oligomers and polymers of heterocyclic conjugated compounds such as polysilane-based, vinylcarbazole-based, thiophene-based and aniline-based compounds.

More specific materials for the hole injection layer 14a or the hole transport layer 14b include α-naphthylphenyl-phenylenediamine (NPD), porphyrin, metallic tetraphenylporphyrin, metallic naphthalocyanine, hexacyanoazatriphenylene, 7,7,8,8-tetracyanoquinodimethane (TCNQ), 7,7,8, 8-tetracyano-2,3,5,6-tetrafluoroquinodimethane (F4-TCNQ), tetracyano-4,4,4-tris[3-methylphenyl(phenyl) amino]tri phenyl amine, N,N,N',N'-tetrakis(p-tolyl)p-phenylenediamine, N,N,N',N'-tetraphenyl-4,4'-diaminobiphenyl, N-phenylcarbazole, 4-di-p-tolylaminostilbene, poly(p-phenylene vinylene), poly (thiophene vinylene) and poly(2,2'-thienylpyrrole), but are not limited to these.

<Light-Emitting Layer>

The light-emitting layer 14c is a region into which holes and electrons are injected from the anode 13 and the cathode 15, respectively, when applying a voltage by the anode 13 and the cathode 15, and in which holes and electrons are further recombined. The light-emitting layer 14c is constituted using the aforementioned organic EL light-emitting material according to an embodiment as a material having high emission efficiency. In addition, the organic EL light-emitting material according to an embodiment may be formed as a pinhole-free film to constitute the light-emitting layer 14c. Since the organic EL light-emitting material has a broad space between the absorption end in the Stokes shift and light emission so as not to exhibit self-quenching, it is also possible to form a thick light-emitting layer 14c. For example, the light-emitting layer 14c is set to have a thickness of 5 nm to 1 µm.

<Electron Transport Layer>

The electron transport layer 14d is a layer for transport electrons injected from the cathode 15 to the light-emitting layer 14c. Examples of the material for the electron transport layer 14d include quinoline, perylene, bis-styryl, pyrazine, triazole, oxazole, oxadiazole, fluorenone, and derivatives thereof. Specifically, there are included tris(8-hydroxyquinoline)aluminum (abbreviated name: Alq3), anthracene, naphthalene, phenanthrene, pyrene, anthracene, perylene, butadiene, coumarin, acridine, stilbene and derivatives thereof.

Each of the above-described layers 14a to 14d constituting the organic layer 14 can be formed, for example, by a vapor deposition method such as sputtering, a spin-coating method, or the like.

The organic layer 14 has a layer construction including at least the light-emitting layer 14c. Further, the organic layer 14 includes the hole transport layer 14b alone (construction shown in FIG. 1) or includes the hole transport layer 14b and the hole injection layer 14a (construction shown in FIG. 2), between the anode 13 and the light-emitting layer 14c.

Further, each of the layers constituting the aforementioned organic layer 14, for example, the hole transport layer 14b, the light-emitting layer 14c or the electron transport layer 14d, may have a stacked structure constituted of multiple layers.

<Cathode>

The cathode 15 has a two-layer structure formed by stacking, for example, a first layer (electron injection layer) 15a and a second layer (negative electrode layer) 15b in this order from the organic layer 14 side.

The first layer 15a is a layer for injecting electrons from the second layer 15b to the electron transport layer 14d. Materials for use in the first layer 15a include alkali earth metal fluorides including, for example, lithium fluoride (LiF) and the like.

Typical examples of the material constituting the second layer 15b include a metal such as Al, Ti, In, Na, K, Mg, Li, Cs, Rb, Ca or Ba, and an alloy composition such as a Mg—Ag alloy or an Al—Li alloy.

The cathode 15 can be formed by such techniques as a vacuum evaporation method, a sputtering method, and a plasma CVD method. When the drive system used for display devices with the organic EL light-emitting elements 11, 11' is an active matrix system, the cathode 15 is formed in a solid film state on the substrate 12 in a condition insulated from the anode 13 by the organic layer 14 and the aforementioned insulating film, which is not shown, and is used as a common electrode of respective pixels.

Meanwhile, needless to say, the structure of the cathode 15 is not limited to the aforementioned one and may have an optimal combination of layers and a stacked structure thereof depending on the structure of a device to be manufactured. For example, the cathode 15 according to the embodiment has a stacked structure having layers with different functions, that is, a stacked structure in which an inorganic layer (first layer 15a) for accelerating the electron injection into the organic layer 14 and an inorganic layer (second layer 15b) for controlling the electrode are separated. However, the inorganic layer for accelerating the electron injection into the organic layer 14 may also function as the inorganic layer for controlling the electrode, or these layers may be provided as a single layer structure. Further, such a single layer structure may have a transparent electrode such as ITO formed thereon.

In general, a direct current is applied to the organic EL light-emitting elements 11, 11' having the aforementioned construction, but a pulsed current or an alternate current may also be used. No particular limitation is imposed on the current value and the voltage value, when these values are within a range in which the elements are not damaged. When taking the power consumption and lifetime of the organic EL light-emitting element into consideration, however, it is desirable to allow the element to emit light by a possible small electric energy with high efficiency.

When the organic EL light-emitting elements 11, 11' have a cavity structure, the total film thickness of the organic layer 14 and the electrode layer (in the embodiment, cathode 15) constituted of a transparent or translucent material is defined by the wavelength of emitting light and is set to be a value introduced from the calculation of multiple interference. When a display device using the organic EL light-emitting elements 11, 11' has a so-called TAC (Top Emitting Adoptive Current drive) structure, in which a top-face emission type organic EL light-emitting element is provided on the substrate on which TFT is formed, it is possible to improve the efficiency of light extracted to the outside and to control the emission spectrum by positively using the cavity structure.

In the organic EL light-emitting elements 11, 11' having the construction as described above, the light-emitting layer 14c of the organic layer 14 is constituted using an organic EL light-emitting material including at least one kind of metal pyrazole complex represented by general formula (1) or (2). This makes it possible to constitute an organic EL light-emitting element having high emission efficiency.

The organic EL light-emitting element according to an embodiment is not limited to the application to a top-face emission type or a TAC structure using the same and is broadly applicable to a construction in which at least an organic layer having a light-emitting layer is inserted between an anode and a cathode. Accordingly, it is also applicable to an element constituted by stacking a cathode, an organic layer and an anode in this order from a substrate side and to a so-called bottom-face emission type organic electroluminescent element in which an electrode located on the substrate side (lower electrode as a cathode or an anode) is formed of a transparent material and an electrode located on the side opposite to the substrate (upper electrode as a cathode or an anode) is formed of a reflective material to allow light to be emitted only from the lower electrode side. Such construction can also produce similar effects to those of the top-face emission type by using an organic EL light-emitting material including at least one kind of metal pyrazole complex represented by general formula (1) or (2) in a light-emitting layer.

Further, the organic EL light-emitting element according to an embodiment may be an element formed by having a pair of electrodes (anode and cathode) and an organic layer inserted between these electrodes. Therefore, the organic EL light-emitting element is not limited to one including only a pair of electrodes and an organic layer, but may include other constituents (for example, an inorganic compound layer and an inorganic component) within a range in which the effect is not impaired.

The organic EL light-emitting element according to an embodiment can be used to constitute display devices such as a flat light source and a color display.

<<Display Device>>

Figure 3:
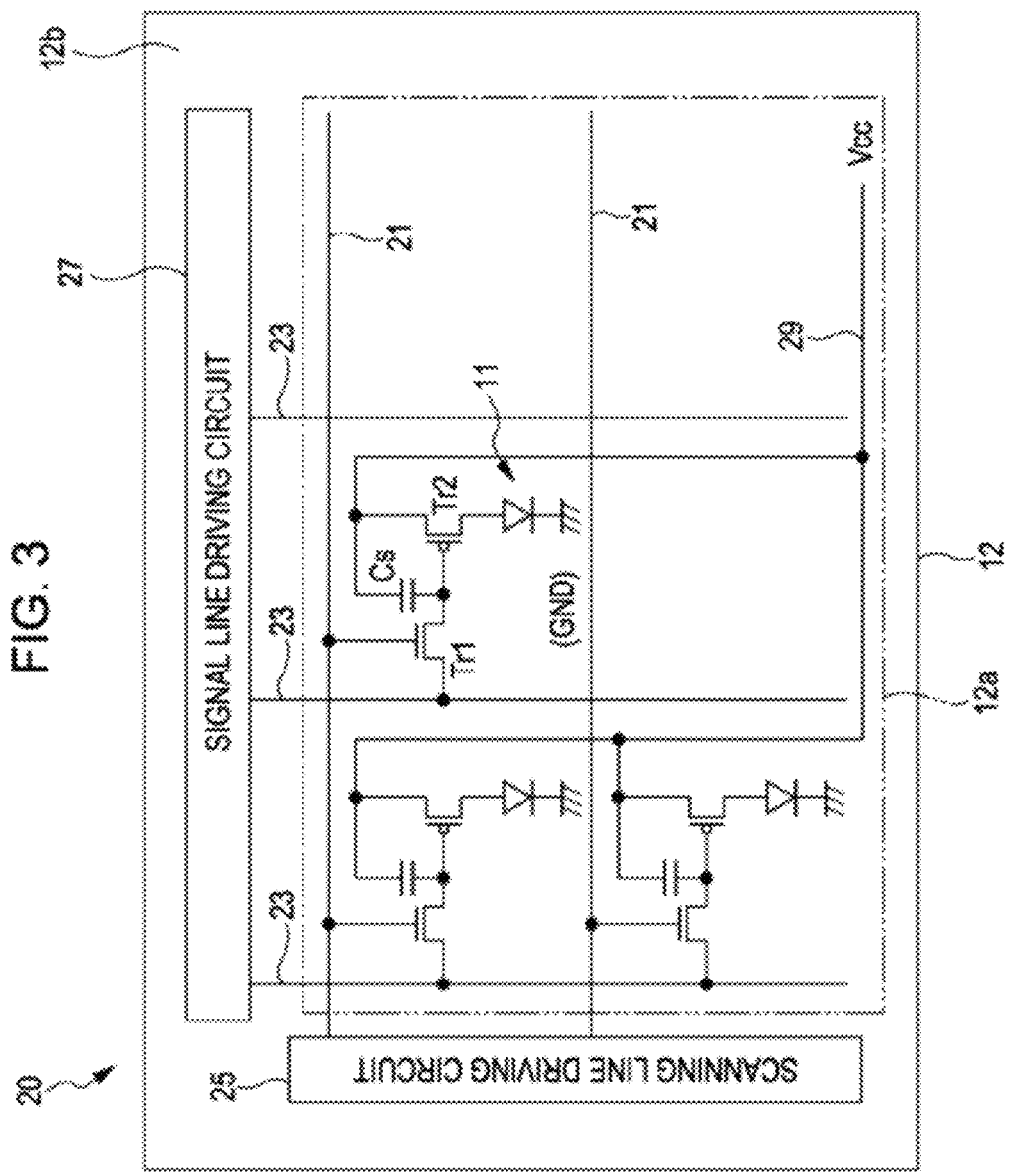
FIG. 3 is a diagram showing one example of a circuit construction of a display device using an organic EL light-emitting element according to an embodiment.

FIG. 3 is a schematic view of a circuit construction for illustrating one constitutional example of a display device using the above-described organic EL light-emitting element, that is, organic EL display device. Here is described an embodiment of a display device 10 of the active matrix system using the organic EL light-emitting element 11 according to an embodiment.

As shown in the drawing, on the substrate 12 of a display device 20, a display region 12a and a peripheral region 12b thereof are defined. The display region 12a is provided with multiple scanning lines 21 and multiple signal lines 23 interconnected transversely and vertically, and one pixel is arranged corresponding to each of portions defined by the crossing lines to constitute a pixel array portion. In the peripheral region 12b are arranged a scanning line driving circuit 25 for scanning and driving scanning lines 21, and a signal line driving circuit 27 for supplying picture signal (that is, input signal) according to luminance information to a signal line 23.

Pixel circuits provided at the respective portions defined by the crossing scanning line 21 and signal line 23 include, for example, a switching thin film transistor Tr1, a driving thin film transistor Tr2, a holding capacitor Cs, and an organic EL light-emitting element 11. Upon driving by the scanning line driving circuit 25, a picture signal written from the signal line 23 via the switching thin film transistor Tr1 is retained in the holding capacitor Cs, electric current corresponding to the amount of the retained signal is supplied from the driving thin film transistor Tr2 to the organic EL light-emitting element 11, and the organic EL light-emitting element 11 emits light with luminance corresponding to the current value. The driving thin film transistor Tr2 and the holding capacitor Cs are connected to a common power supply line (Vcc) 29.

The aforementioned construction of the pixel circuit is one example, and if necessary, a pixel circuit may include a capacitive element therein, and further include multiple transistors. Further, a driving circuit may be added to the peripheral region 12b in accordance with the change of the pixel circuit.

In the display device 20 according to an embodiment, the organic EL light-emitting element 11 according to an embodiment described in FIG. 1 is provided to one pixel as an organic EL light-emitting element of red (R), green (G) or blue (B) to form a subpixel. The subpixels of three colors constitute a unit pixel. Then, pixels each including sub-pixels of three colors are arranged on the substrate 12 to perform full color display.

Further, in the display device 20 including the organic EL light-emitting element 11 having such construction, it is preferable to perform such treatment as forming a sealing film for preventing the degradation of the organic EL light-emitting element 11 caused by moisture, oxygen and the like in the atmosphere.

In place of the organic EL light-emitting element 11, the organic EL light-emitting element 11' according to an embodiment described in FIG. 2 may be used.

In the display device 20 having the above-described construction, since the organic EL light-emitting element constituting a display device has high emission efficiency as described above, by combining the organic EL light-emitting element as organic EL light-emitting elements emitting blue, green and red rays of light, respectively, it becomes possible to attain full color display having high color reproduction and reliability.

EXAMPLES

Hereinafter, Examples of organic EL light-emitting elements using the organic EL light-emitting material defined in an embodiment are described specifically.

Example 1

An organic EL light-emitting element in Example 1 was produced by procedures below. Here, the construction of the organic EL light-emitting element in FIG. 1 was given.

First, on the substrate 12 of a flat glass plate, an IWO transparent conductive film having a thickness of 100 nm was formed as an anode 13 to produce a cell for an organic EL light-emitting element for top-face emission.

Next, as a hole transport layer 14b, a film composed of α-NPD as represented by a structural formula (A) below was formed in a thickness of 40 nm. Here, α-NPD denotes N,N'-bis(1-naphthyl)-N,N'-diphenyl[1,1'-biphenyl]-4,4'-diamine.

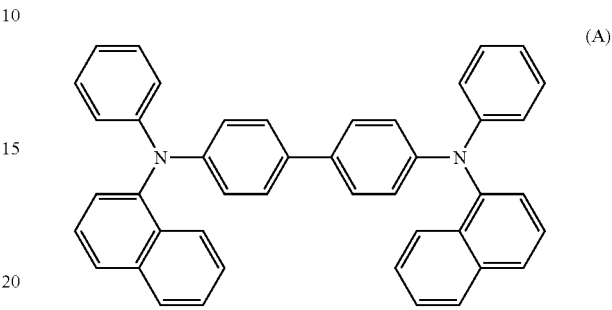

(A)

On the hole transport layer 14b thus formed, the light-emitting layer 14c composed of the organic EL light-emitting material according to an embodiment was formed. In the Example, a compound (I) produced according to a method below was used.

[Compound (I)]

In an argon atmosphere, 3,5-dimethylpyrazole (480 mg, 5.0 mmol) and $[Cu(CH_3CN)_4][PF_6]$ (1.86 g, 5.0 mmol) were dissolved in dry THF (18.0 mL), which was stirred at room temperature. After 5-minute stirring, 0.70 mL (5.0 mmol) of triethylamine (one obtained by distilling from KOH and being dried) was added slowly. Immediately, white precipitates generated, which was additionally stirred for 6 hours. The generated white crystal was filtrated with a glass filter, and the crystal was washed with a small amount of dry methylene chloride. By performing vacuum drying, a white crystal was obtained. The yield at this time was 702 mg (yield: 88%). Tris[3,5-dimethylpyazolate Copper (I)] complex, $\{[3,5-(CH_3)_2Pz]Cu\}_3$, obtained by finally performing sublimation and purification two times was defined as the compound (I). The structural formula (I) thereof is shown below. That is, in the aforementioned formula (1), $R_1$ and $R_3$ are $CH_3$, $R_2$ is H, n=3, and M=Cu.

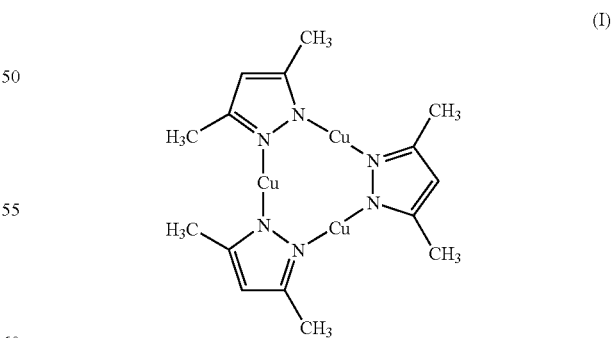

(I)

Here, the compound (I) was vapor-deposited to form a film having a thickness of 30 nm.

Next, as the electron transport layer 14d, Alq3 (8-hydroxyquinoline aluminum) shown by a structural formula (B) below was vapor-deposited to form a film having a thickness of 30 nm.

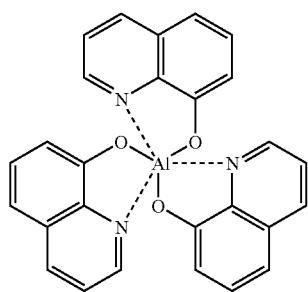

(B)

After that, as the first layer 15a of the cathode 15, a film constituted of LiF was formed by vapor deposition in a thickness of 0.35 nm, and finally, as the second layer 15b of the cathode 15, a film constituted of Al was formed by vapor deposition in a thickness of 250 nm.

Example 2

An organic EL light-emitting element was produced under the same conditions as those in Example 1, except that the light-emitting layer 14c having a thickness of 30 nm was formed using compound (II) produced through a method below in place of the compound (I).

[Compound (II)]

In an argon atmosphere, 3,5-di-trifluoro-pyrazole (754 mg, 3.68 mmol) and $Cu_2O$ (290 mg, 1.90 mmol) were suspended in dry acetonitrile (0.25 mL) and dry toluene (10 mL), which was stirred overnight at 60° C. After removing unnecessary residues by ultrafiltration and distilling the solvent away under a reduced pressure, the filtrate was recrystallized from dry hexane. The yield at that time was 0.785 mg (yield: 52%). Tris[3,5-bis(trifluoromethyl)pyazolate Copper(I)] complex, $\{[3,5\text{-}(CF_3)_2Pz]Cu\}_3$, obtained by finally performing sublimation and purification two times was defined as the compound (II). The structural formula (II) thereof is shown below. That is, in the aforementioned general formula (1), $R_1$ and $R_3$ are $CF_3$, $R_2$ is H, n=3, and M=Cu.

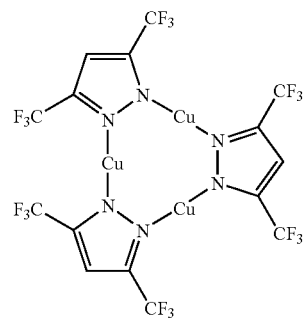

(II)

Comparative Example 1

A sample in Comparative Example 1 was produced under the same conditions as those in Example 1, except that the hole transport layer 14b and the light-emitting layer 14c were omitted and the thickness of the electron transport layer 14d (Alq3) was changed to 50 nm.

Comparative Example 2

A sample in Comparative Example 2 was produced under the same conditions as those in Example 1, except that the light-emitting layer 14c and the electron transport layer 14d were omitted.

Comparative Example 3

A sample in Comparative Example 3 was produced under the same conditions as those in Example 1, except that the light-emitting layer 14c was omitted and the thickness of the electron transport layer 14d (Alq3) was changed to 60 nm.

Comparative Example 4

A sample in Comparative Example 4 was produced under the same conditions as those in Example 1, except that the hole transport layer 14b and the electron transport layer 14d were omitted and the thickness of the light-emitting layer 14c (compound (I)) was changed to 40 nm.

Figure 4:
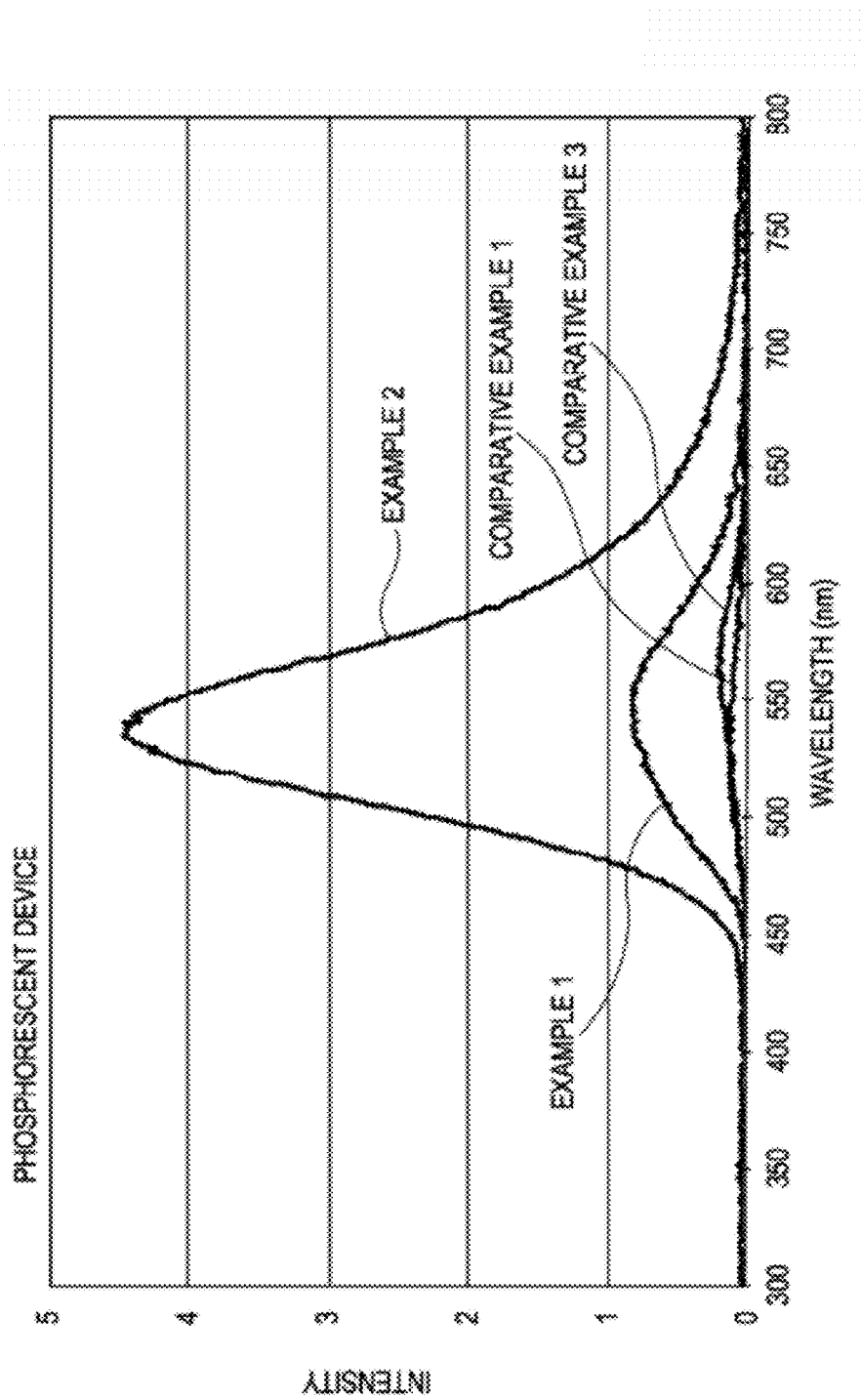
FIG. 4 is a diagram showing measurement results of the emission spectrum of organic EL light-emitting elements in Examples 1, 2.
Figure 5:
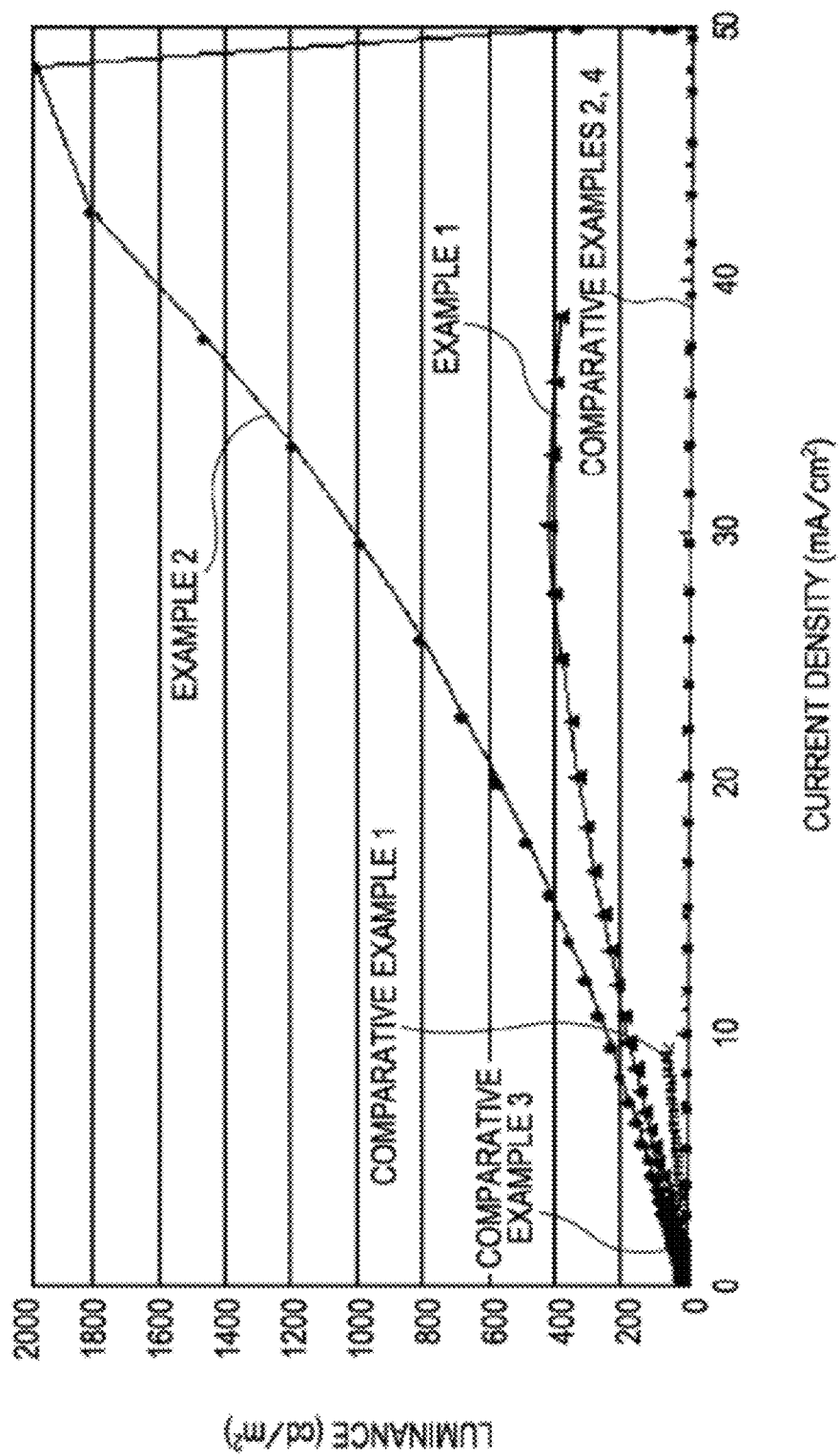
FIG. 5 is a diagram showing the relationship between the current density and the luminance of organic EL light-emitting elements in Examples 1, 2.

For each of the obtained samples, a current density, luminance and an emission spectrum when a drive voltage in Table 1 was applied were measured. The current density and the luminance are shown in Table 1, and the emission spectrum is shown in FIG. 4. Note that, FIG. 4 shows results only for samples in Examples 1 and 2 and Comparative Examples 1 and 3, where emission was perceived. FIG. 5 shows the relationship between the current density and the luminance at that time.

TABLE 1

| Sample Name | Voltage (V) | Current (mA/cm$^2$) | Luminance (cd/m$^2$) |
|---|---|---|---|
| Example 1 | 28.5 | 30.23 | 415.4 |
| Example 2 | 28 | 48.42 | 1985 |
| Comparative Example 1 | 10 | 9.35 | 61.6 |
| Comparative Example 2 | 10 | 20.24 | 0 |
| Comparative Example 3 | 30 | 4.16 | 94.9 |
| Comparative Example 4 | 10 | 37.1 | 0 |

From the results, by stacking the hole transport layer 14b, the light-emitting layer 14c constituted of the organic EL light-emitting element according to an embodiment, and the electron transport layer 14d, as in Examples 1, 2, the improvement in the electroconductivity was recognized (in Table 1) and an emission (phosphorescence) having a peak of the emission intensity at the wavelength of 540 to 550 nm was recognized (FIG. 4). Further, as compared with Comparative Examples, the luminance at the same current density was significantly improved (FIG. 5).

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An organic EL light-emitting material comprising at least one kind of metal pyrazole complex represented by one of general formulae (1) and (2):

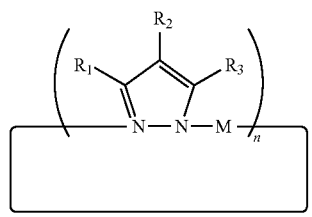

wherein at least one of $R_1$, $R_2$, and $R_3$ represents a branched alkyl group having 1 to 18 carbon atoms, and any remaining ones of $R_1$, $R_2$, and $R_3$ independently represent a hydrogen atom, a branched or linear alkyl group having 1 to 18 carbon atoms, a branched or linear halogen-substituted alkyl group having 1 to 18 carbon atoms, a phenyl group, a halogen-substituted phenyl group, a halogen atom, an ester group having 1 to 12 carbon atoms, an alkyl sulfide group, an ether group or an amide group; n represents an integer of 3 to 6; and M is selected from Au, Ag and Cu,

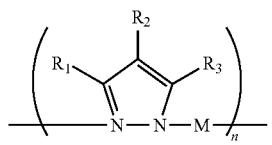

wherein at least one of $R_1$, $R_2$, and $R_3$ represents a branched alkyl group having 1 to 18 carbon atoms, and any remaining ones of $R_1$, $R_2$, and $R_3$ independently represent a hydrogen atom, a branched or linear alkyl group having 1 to 18 carbon atoms, a branched or linear halogen-substituted alkyl group having 1 to 18 carbon atoms, a phenyl group, a halogen-substituted phenyl group, a halogen atom, an ester group having 1 to 12 carbon atoms, an alkyl sulfide group, an ether group or an amide group; n represents a positive integer; and M is selected from Au, Ag and Cu.

2. The organic EL light-emitting material according to claim 1, wherein for general formulae (1) and (2), at least one of R1, R2, and R3 is a hydrogen atom.

3. The organic EL light-emitting material according to claim 1, wherein for general formulae (1) and (2), M is Au.

4. The organic EL light-emitting material according to claim 1, wherein for general formulae (1) and (2), M is Ag.

5. An organic EL light-emitting element comprising:
a hole transport layer;
a light-emitting layer including organic EL light-emitting material composed of at least one kind of metal pyrazole complex represented by one of general formulae (1) and (2); and
an electron transport layer between an anode and a cathode provided on a substrate, in this order from the anode side;

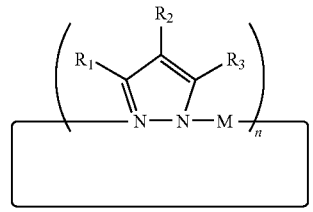

wherein at least one of $R_1$, $R_2$, and $R_3$ represents a branched alkyl group having 1 to 18 carbon atoms, and any remaining ones of $R_1$, $R_2$, and $R_3$ independently represent a hydrogen atom, a branched or linear alkyl group having 1 to 18 carbon atoms, a branched or linear halogen-substituted alkyl group having 1 to 18 carbon atoms, a phenyl group, a halogen-substituted phenyl group, a halogen atom, an ester group having 1 to 12 carbon atoms, an alkyl sulfide group, an ether group or an amide group; n represents an integer of 3 to 6; and M is selected from Au, Ag and Cu,

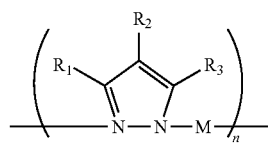

wherein at least one of $R_1$, $R_2$, and $R_3$ represents a branched alkyl group having 1 to 18 carbon atoms, and any remaining ones of $R_1$, $R_2$, and $R_3$ independently represent a hydrogen atom, a branched or linear alkyl group having 1 to 18 carbon atoms, a branched or linear halogen-substituted alkyl group having 1 to 18 carbon atoms, a phenyl group, a halogen-substituted phenyl group, a halogen atom, an ester group having 1 to 12 carbon atoms, an alkyl sulfide group, an ether group or an amide group; n represents a positive integer; and M is selected from Au, Ag and Cu.

6. The organic EL light-emitting element according to claim 5 further comprising a hole injection layer between the anode and the hole transport layer.

7. An organic EL light-emitting material comprising at least one kind of metal pyrazole complex represented by one of general formulae (1) and (2):

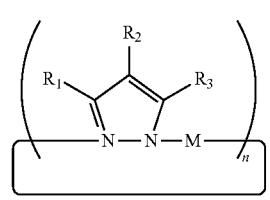

wherein $R_1$, $R_2$, and $R_3$ independently represent a hydrogen atom, a branched alkyl group having 1 to 18 carbon atoms, a branched or linear halogen-substituted alkyl group having 1 to 18 carbon atoms, a phenyl group, a halogen-substituted phenyl group, a halogen atom, an ester group having 1 to 12 carbon atoms, an alkyl sulfide group, an ether group or an amide group; n represents an integer of 3 to 6; and M is selected from Au, Ag and Cu,

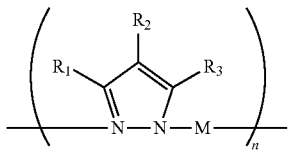
(2)

wherein $R_1$, $R_2$, and $R_3$ independently represent a hydrogen atom, a branched alkyl group having 1 to 18 carbon atoms, a branched or linear halogen-substituted alkyl group having 1 to 18 carbon atoms, a phenyl group, a halogen-substituted phenyl group, a halogen atom, an ester group having 1 to 12 carbon atoms, an alkyl sulfide group, an ether group or an amide group; n represents a positive integer; and M is selected from Au, Ag and Cu.

8. An organic EL light-emitting material comprising at least one kind of metal pyrazole complex represented by one of general formulae (1) and (2):

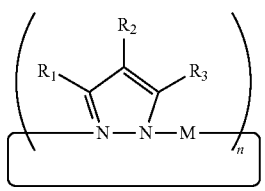
(1)

wherein at least one of $R_1$, $R_2$, and $R_3$ represents an ester group having 1 to 12 carbon atoms, and any remaining ones of $R_1$, $R_2$, and $R_3$ independently represent a hydrogen atom, a branched or linear alkyl group having 1 to 18 carbon atoms, a branched or linear halogen-substituted alkyl group having 1 to 18 carbon atoms, a phenyl group, a halogen-substituted phenyl group, a halogen atom, an ester group having 1 to 12 carbon atoms, an alkyl sulfide group, an ether group or an amide group; n represents an integer of 3 to 6; and M is selected from Au, Ag and Cu,

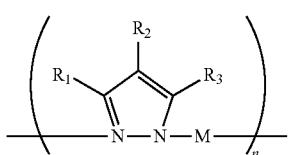
(2)

wherein at least one of $R_1$, $R_2$, and $R_3$ represents an ester group having 1 to 12 carbon atoms, and any remaining ones of $R_1$, $R_2$, and $R_3$ independently represent a hydrogen atom, a branched or linear alkyl group having 1 to 18 carbon atoms, a branched or linear halogen-substituted alkyl group having 1 to 18 carbon atoms, a phenyl group, a halogen-substituted phenyl group, a halogen atom, an ester group having 1 to 12 carbon atoms, an alkyl sulfide group, an ether group or an amide group; n represents a positive integer; and M is selected from Au, Ag and Cu.

9. An organic EL light-emitting material comprising at least one kind of metal pyrazole complex represented by one of general formulae (1) and (2):

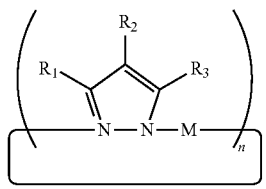
(1)

wherein at least one of $R_1$, $R_2$, and $R_3$ represents an alkyl sulfide group, and any remaining ones of $R_1$, $R_2$, and $R_3$ independently represent a hydrogen atom, a branched or linear alkyl group having 1 to 18 carbon atoms, a branched or linear halogen-substituted alkyl group having 1 to 18 carbon atoms, a phenyl group, a halogen-substituted phenyl group, a halogen atom, an ester group having 1 to 12 carbon atoms, an alkyl sulfide group, an ether group or an amide group; n represents an integer of 3 to 6; and M is selected from Au, Ag and Cu,

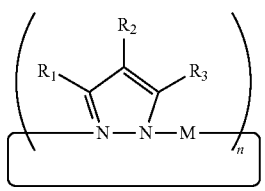
(2)

wherein at least one of $R_1$, $R_2$, and $R_3$ represents an alkyl sulfide group, and any remaining ones of $R_1$, $R_2$, and $R_3$ independently represent a hydrogen atom, a branched or linear alkyl group having 1 to 18 carbon atoms, a branched or linear halogen-substituted alkyl group having 1 to 18 carbon atoms, a phenyl group, a halogen-substituted phenyl group, a halogen atom, an ester group having 1 to 12 carbon atoms, an alkyl sulfide group, an ether group or an amide group; n represents a positive integer; and M is selected from Au, Ag and Cu.

10. An organic EL light-emitting material comprising at least one kind of metal pyrazole complex represented by one of general formulae (1) and (2):

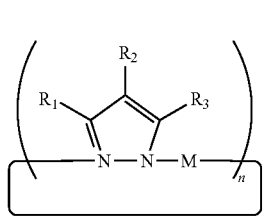
(1)

wherein at least one of $R_1$, $R_2$, and $R_3$ represents an ether group, and any remaining ones of $R_1$, $R_2$, and $R_3$ independently represent a hydrogen atom, a branched or linear alkyl group having 1 to 18 carbon atoms, a branched or linear halogen-substituted alkyl group having 1 to 18 carbon atoms, a phenyl group, a halogen-substituted phenyl group, a halogen atom, an ester group having 1 to 12 carbon atoms, an alkyl sulfide group, an ether group or an amide group; n represents an integer of 3 to 6; and M is selected from Au, Ag and Cu,

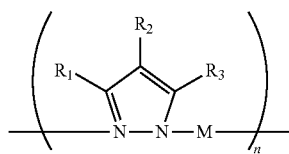

(2)

wherein at least one of $R_1$, $R_2$, and $R_3$ represents an ether group, and any remaining ones of $R_1$, $R_2$, and $R_3$ independently represent a hydrogen atom, a branched or linear alkyl group having 1 to 18 carbon atoms, a branched or linear halogen-substituted alkyl group having 1 to 18 carbon atoms, a phenyl group, a halogen-substituted phenyl group, a halogen atom, an ester group having 1 to 12 carbon atoms, an alkyl sulfide group, an ether group or an amide group; n represents a positive integer; and M is selected from Au, Ag and Cu.

11. An organic EL light-emitting material comprising at least one kind of metal pyrazole complex represented by one of general formulae (1) and (2):

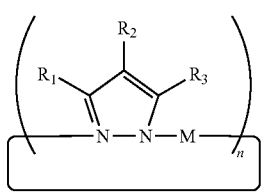

(1)

wherein at least one of $R_1$, $R_2$, and $R_3$ represents an amide group, and any remaining ones of $R_1$, $R_2$, and $R_3$ independently represent a hydrogen atom, a branched or linear alkyl group having 1 to 18 carbon atoms, a branched or linear halogen-substituted alkyl group having 1 to 18 carbon atoms, a phenyl group, a halogen-substituted phenyl group, a halogen atom, an ester group having 1 to 12 carbon atoms, an alkyl sulfide group, an ether group or an amide group; n represents an integer of 3 to 6; and M is selected from Au, Ag and Cu,

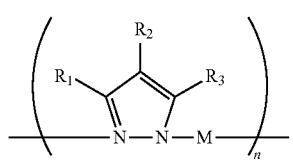

(2)

wherein at least one of $R_1$, $R_2$, and $R_3$ represents an amide group, and any remaining ones of $R_1$, $R_2$, and $R_3$ independently represent a hydrogen atom, a branched or linear alkyl group having 1 to 18 carbon atoms, a branched or linear halogen-substituted alkyl group having 1 to 18 carbon atoms, a phenyl group, a halogen-substituted phenyl group, a halogen atom, an ester group having 1 to 12 carbon atoms, an alkyl sulfide group, an ether group or an amide group; n represents a positive integer; and M is selected from Au, Ag and Cu.

12. An organic EL light-emitting material comprising at least one kind of metal pyrazole complex represented by one of general formulae (1) and (2):

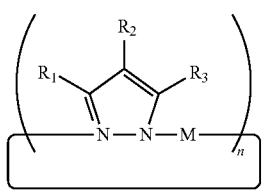

(1)

wherein at least one of $R_1$, $R_2$, and $R_3$ represents a branched or linear halogen-substituted alkyl group having 1 to 18 carbon atoms, a phenyl group, a halogen-substituted phenyl group, or a halogen atom, and any remaining ones of $R_1$, $R_2$, and $R_3$ independently represent a hydrogen atom, a branched or linear alkyl group having 1 to 18 carbon atoms, a branched or linear halogen-substituted alkyl group having 1 to 18 carbon atoms, a phenyl group, a halogen-substituted phenyl group, a halogen atom, an ester group having 1 to 12 carbon atoms, an alkyl sulfide group, an ether group or an amide group; n represents an integer of 3 to 6; and M is selected from Au, Ag and Cu,

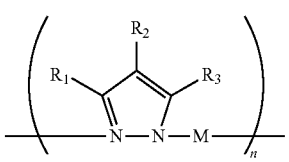

(2)

wherein at least one of $R_1$, $R_2$, and $R_3$ represents a branched or linear halogen-substituted alkyl group having 1 to 18 carbon atoms, a phenyl group, a halogen-substituted phenyl group, or a halogen atom, and any remaining ones of $R_1$, $R_2$, and $R_3$ independently represent a hydrogen atom, a branched or linear alkyl group having 1 to 18 carbon atoms, a branched or linear halogen-substituted alkyl group having 1 to 18 carbon atoms, a phenyl group, a halogen-substituted phenyl group, a halogen atom, an ester group having 1 to 12 carbon atoms, an alkyl sulfide group, an ether group or an amide group; n represents a positive integer; and M is selected from Au, Ag and Cu.

13. The organic EL light-emitting material according to claim 12, wherein for general formulae (1) and (2), at least one of $R_1$, $R_2$, and $R_3$ represents a branched or linear halogen-substituted alkyl group having 1 to 18 carbon atoms.

14. The organic EL light-emitting material according to claim 12, wherein for general formulae (1) and (2), at least one of $R_1$, $R_2$, and $R_3$ represents a phenyl group.

15. The organic EL light-emitting material according to claim 12, wherein for general formulae (1) and (2), at least one of $R_1$, $R_2$, and $R_3$ represents a halogen-substituted phenyl group.

16. The organic EL light-emitting material according to claim 12, wherein for general formulae (1) and (2), at least one of $R_1$, $R_2$, and $R_3$ represents a halogen atom.

* * * * *